Nov. 22, 1927. Re. 16,792

J. G. HOMAN

DEVICE FOR RETAINING HERNIAL SUPPORTING PADS IN PLACE

Original Filed Jan. 17, 1925

INVENTOR

John G. Homan

By his attorneys

Byrnes, Townsend & Parmelee

Reissued Nov. 22, 1927. Re. 16,792

UNITED STATES PATENT OFFICE.

JOHN GREENLEAF HOMAN, OF STEUBENVILLE, OHIO.

DEVICE FOR RETAINING HERNIAL SUPPORTING PADS IN PLACE.

Original No. 1,580,729, dated April 13, 1926, Serial No. 3,054, filed January 17, 1925. Application for reissue filed July 1, 1926. Serial No. 119,981.

This invention is for means for retaining a supporting pad or like therapeutic device in place and especially relates to a device to be used in connection with present forms of hernial trusses and body supports.

With present forms of supporting pads and similar hernial supporting devices difficulty is experienced in retaining the pad in just the right position to properly support the injury. It is known that if the support is applied at exactly the correct place a much smaller pad and a more comfortable and lighter outfit may be used. It is believed furthermore that the opportunity for cure is enhanced if the support is properly retained in the correct position and cannot slip.

At the same time, the support cannot be permanently secured to the body of the wearer, and it must be conveniently removable, when necessary or desirable.

The present invention has for its principal object to provide means for holding the pad of supports of this or similar nature in place, and for preventing them from slipping, and which will permit of the easy removal of the pad when desired.

The invention may be readily understood by reference to the accompanying drawings, which are illustrative of a preferred embodiment of the invention, but to the details of which I do not limit myself, as various modifications may be made within the spirit of the invention. In the drawings.

Figure 1:
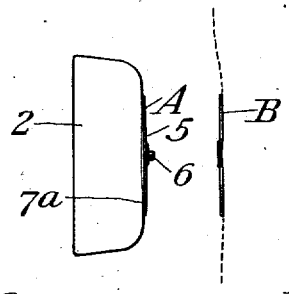
Figure 1 is a side elevation of a pad having the invention applied thereto, and showing a separable element of the invention detached therefrom.
Figure 2:
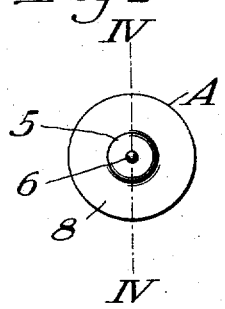
Figure 2 is a front view of one member separated from the pad.
Figure 3:
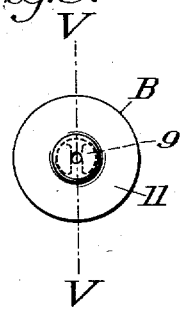
Figure 3 is a similar view of the cooperating separable member.
Figure 4:
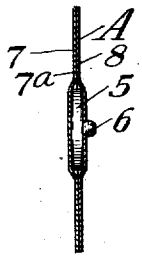
Figure 4 is a vertical section through one member.

According to my invention, it is proposed to preferably secure the pad in place by a separable fastening means having adhesive on the outer faces thereof. One element of the separable fastener may thus be stuck to the pad and the other member may be secured to the body of the wearer at just the proper point, to hold the pad in place when the two members are connected.

In the drawings, 2 designates any usual or preferred pad for supporting a part of the body. One part of the pad supporting means is attached to the pad, and is designated A, while the other part is designated B.

In the form illustrated, member A comprises the stud member 5 of a separable snap fastener or button having a stud portion 6. This fastener member is confined between two fabric disks or other shaped members, 7 and 8, preferably formed of adhesive tape or surgical adhesive. The disk 7, at the back face of the button, has its adhesive surface $7^a$ exposed, while disk 8, which is perforated to permit of the passage of the stud of the button therethrough, has its adhesive surface on the inside, so that it adheres to the other disk and holds the two disks together. The finished article is a snap button having an adhesive mounting on the back thereof and having a non-adhesive front surface through which the stud projects.

The member B is generally similar, being composed of the socket member 9 of a snap fastener disposed between similarly arranged suitably shaped adhesive members, such as disks 10, and 11, the back disk 10 having its adhesive surface exposed, and disk 11 being centrally perforated and having its adhesive surface turned in.

In use, the member A is secured to or connected with the supporting pad 2 through its adhesive surface. I have shown in Figure 1 the member A stuck directly on the pad. The member B is then stuck to the body of the wearer at just the right position with respect to the part of the body to be supported, so as to properly hold the pad thereto when the cooperating parts of the separable fastener are in engagement.

In this manner the pad may be held in exactly the proper place without slipping. At the same time the pad can be easily removed by simply separating the fastener. The device can be made cheaply enough so that renewals can frequently be made without appreciable expense.

If desired, the fastening means A could be more permanently secured to the pad, and only the member B would then have to be removed, with the member A removable, it can be accurately applied in the most comfortable and desirable position, and it can be secured by anyone to present types of trusses or body supporting and treating devices.

Figure 6:
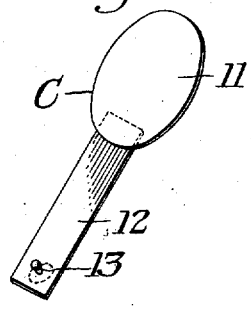
Figure 6 shows a slightly modified form.
Figure 5:
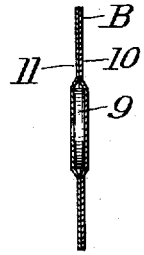
Figure 5 is a vertical section through the other member.

In Figure 6 I have shown one slightly modified form which may be desirable in some cases. The member C is the portion of the unit adapted to attach to the body of the wearer, and has a disk-like or other suitably shaped body 11, adhesive on one side and non-adhesive on the other. Secured to this is a flexible tape 12 carrying an element 13 of a separable fastener. This arrangement enables the pad, which will carry a cooperating fastener part as described, to be applied with greater ease.

I have illustrated a preferred form of the invention, but obviously various changes and modifications can be made therein within the contemplation of the invention, and under the scope of the appended claims.

I claim:

1. The combination with a therapeutic device, of a two part separable fastener for retaining the device in the position where it is worn, said fastener having one part thereof carried on the device and having the other part thereof supported by an adhesive coated sheet which may be stuck in a proper position to support the device.

2. The combination with a supporting pad, of a two part separable fastener having one part secured to the pad and having another part secured to an adhesive coated sheet by means of which the pad may be secured in position to give maximum benefit to the body of the user.

3. In a device of the character described, a two-part separable fastener having cooperating members, each member having a portion adapting it for cooperation with the other and also having an adhesive area, said areas being turned away from each other when the two cooperating elements are together.

4. In a device of the character described, a separable fastener comprised of cooperating parts, one of which is carried on an adhesive coated sheet while the other is attached to an article to be held against a portion of the body.

5. The combination with a therapeutic device, of a two-part separable fastener having one part thereof attached thereto and having its other part provided with an adhesive coated surface.

6. The combination with a device of the class described of means for holding the device from slipping including a member attached thereto at its inner side, a second member having an adhesive surface for attachment to the body of the wearer, and a separable connection between the two members.

7. The combination with a support for a part of the body, of means for holding the support in place including a member having an adhesive surface by which it is connected with the support, a second member having an adhesive surface for attachment to the body of a wearer, and cooperating elements of a separable fastener carried by said members.

8. Supporting means comprising a two-part separable fastener having two cooperating separable members, and a mounting for each member having an exposed adhesive surface thereon.

9. The combination with a body supporting pad, of one part of a separable fastener secured to the pad, an adhesive member for attachment to the body of the wearer, and a cooperating part of the fastener attached to the adhesive member.

10. The combination with a pad, of a separable fastener composed of two cooperating members, each member having a portion adapting it for connection with the other and provided with an adhesive area, said areas being turned away from each other when the two cooperating elements are together.

In testimony whereof, I have hereunto set my hand.

JOHN G. HOMAN.